(12) United States Patent
Do Nascimento et al.

(10) Patent No.: US 9,974,734 B2
(45) Date of Patent: May 22, 2018

(54) COSMETIC COMPOSITION FOR MOISTURIZING KERATINIC TISSUE

(71) Applicant: Natura Cosméticos S.A., São Paulo (BR)

(72) Inventors: Selma Do Nascimento, São Paulo (BR); Marcos Rogério Spina, São Paulo (BR); Daniele Cristina Zulim Botega, Sorocaba (BR); Cristiane Rodrigues Da Silva Pacheco, Sorocaba (BR); Cecilia Nogueira, Sorocaba (BR); Mário Luiz Mathias Netto, Sorocaba (BR)

(73) Assignee: NATURA COSMÉTICOS S.A., São Paulo (BR)

( * ) Notice: Subject to any disclaimer, the term of this patent is extended or adjusted under 35 U.S.C. 154(b) by 336 days.

(21) Appl. No.: 14/984,799

(22) Filed: Dec. 30, 2015

(65) Prior Publication Data
US 2017/0189324 A1 Jul. 6, 2017

(51) Int. Cl.

| | |
|---|---|
| *A61K 36/00* | (2006.01) |
| *A61K 8/97* | (2017.01) |
| *A61K 8/19* | (2006.01) |
| *A61K 8/37* | (2006.01) |
| *A61K 8/41* | (2006.01) |
| *A61K 8/49* | (2006.01) |
| *A61K 8/58* | (2006.01) |
| *A61K 8/60* | (2006.01) |
| *A61K 8/73* | (2006.01) |
| *A61K 8/81* | (2006.01) |
| *A61K 8/92* | (2006.01) |
| *A61Q 19/00* | (2006.01) |
| *A61K 8/34* | (2006.01) |
| *A61K 8/67* | (2006.01) |

(52) U.S. Cl.
CPC ............... *A61K 8/97* (2013.01); *A61K 8/19* (2013.01); *A61K 8/345* (2013.01); *A61K 8/37* (2013.01); *A61K 8/375* (2013.01); *A61K 8/41* (2013.01); *A61K 8/49* (2013.01); *A61K 8/498* (2013.01); *A61K 8/4946* (2013.01); *A61K 8/585* (2013.01); *A61K 8/60* (2013.01); *A61K 8/678* (2013.01); *A61K 8/732* (2013.01); *A61K 8/737* (2013.01); *A61K 8/8147* (2013.01); *A61K 8/922* (2013.01); *A61Q 19/007* (2013.01); *A61K 2800/591* (2013.01)

(58) Field of Classification Search
CPC ...................................... A61K 36/00
USPC .......................................... 424/725
See application file for complete search history.

(56) References Cited

U.S. PATENT DOCUMENTS 8,551,508 B2 * 10/2013 Lee ................. A61K 8/22
424/401

* cited by examiner

*Primary Examiner* — Michael V Meller
(74) *Attorney, Agent, or Firm* — B. Aaron Schulman, Esq.; Stites & Harbison, PLLC (57) ABSTRACT

The present invention is directed to a cosmetic composition comprising (a) an emulsifier selected from: (i) glyceryloleate citrate combined with a native oil as a viscosity modifier; or (ii) organogel comprising *Helianthus Annuus* (Sunflower) Seed Oil, Polyacrylic Acid, Xylityl Sesquicaprylate, Glyceryl Stearate, *Euphorbia Cerifera* (Candelilla) Wax, Sodium Hydroxide and Tocopherol; (b) at most 3 (three) emollient agents; (c) 01 (one) humectant and (d) cosmetically acceptable adjuvants. Furthermore, the present invention is directed to the use of the cosmetic composition according to the present invention as a moisturizing agent to be used on keratinic tissue, particularly skin, and to a method of moisturizing keratinic tissue, particularly skin, comprising applying the cosmetic composition according to the present invention onto said keratinic tissue, particularly skin.

1 Claim, 13 Drawing Sheets

| Attribute | Formula 4 | Formula 5 | Formula 6 | PR4 | PR5 | PR6 | PR7 |
|---|---|---|---|---|---|---|---|
| Spreadability | | | | | | | |
| Sliding | | | | | | | |
| Stickiness | | | | | | | |
| White residue | | | | | | | |
| Velvet film | | | | | | | |
| Dry touch | | | | | | | |
| Immediate brightness | | | | | | | |
| Residual brightness | | | | | | | |
| Immediate oiliness | | | | | | | |
| Residual oiliness | | | | | | | |
| Immediate greasy film | | | | | | | |
| Residual greasy film | | | | | | | |

| Color | | | | | |
|---|---|---|---|---|---|
| Intensity | Low | Medium-low | Medium | Medium-high | High |

| Atribute | Formula 7 | Formula 8 | Formula 9 | PR8 | PR9 | PR10 | PR11 | P R12 |
|---|---|---|---|---|---|---|---|---|
| Spreadability | | | | | | | | |
| Sliding | | | | | | | | |
| Stickiness | | | | | | | | |
| White residue | | | | | | | | |
| Velvet film | | | | | | | | |
| Dry touch | | | | | | | | |
| Immediate brightness | | | | | | | | |
| Residual brightness | | | | | | | | |
| Immediate oiliness | | | | | | | | |
| Residual oiliness | | | | | | | | |
| Immediate greasy film | | | | | | | | |
| Residual greasy film | | | | | | | | |

| Color Intensity | Low (0 – 2.0) | Medium-low (2.1 – 4.0) | Medium (4.1 – 6.0) | Medium-high (6.1 – 8.0) | High (8.1 – 10.0) |
|---|---|---|---|---|---|

COSMETIC COMPOSITION FOR MOISTURIZING KERATINIC TISSUE

The invention relates to a new emulsifying technology for body moisturizers based on minimalist compositions, thus decreasing the environmental impact. In another aspect, the present invention relates to moisturizer compositions and also their use on keratinic tissue, particularly skin. Finally, the invention relates to a method of moisturizing keratinic tissue by applying on the mentioned tissue the composition according to the present application.

BACKGROUND OF THE INVENTION

Prior art document WO 2014/147447 describes a process for preparing cosmetic compositions at two stages. The first relates to the preparation of organogels in which liquid oils are structured by a mixture of structuring agents such as monoglycerides and waxes, which also have the addition of other components such as polymers and polyol esters. The second step is the formation of the cold or hot process cosmetic compositions where emulsions are prepared by the addition of water, aqueous solutions and other components, to the organogel. The emulsions prepared have superior sensory, chemical-physical and stability characteristics, to those currently produced by the classic technology of preparation with emulsifiers.

Prior art document EP 1 641 904 relates to a O/W emulsifier, containing 70 to 90% by weight glyceryloleate citrate and 10 to 30% by weight of a viscosity modifier with a viscosity in the range from 1 to 10,000 mPas, characterized in that the viscosity modifier is a native oil. The viscosity modifier being a caprylic/capric triglyceride. Also, the use of glyceryloleate citrate or of an O/W emulsifier in cosmetic or dermatological compositions is also disclosed.

Finally, prior art document EP 2 883 536 disclose a cosmetic agent containing a suitable carrier in each case related to the total weight of the agent; one or more liquid oils; one or more waxes with a fusion point from 20 to 90° C.; at least one emulsifying agent, selected from the emulsifying agents with the INCI designation "Glyceryl Oleates citrate, Caprylic/Capric Triglyceride", "Polyglyceryl-4 Laurate/Succinate", "Polyglyceryl-4 Laurate/Sebacate (and) Polyglyceryl-4 Caprylate/Caprate", "Glyceryl Stearate (and) Polyglyceryl-6 of Palmitate/Succinate (and) Cetearyl Alcohol Polyglyceryl-4 Laurate/Sebacate (and) Polyglyceryl-6 Caprylate/Caprate" as well as their mixtures and if necessary further ingredients, characterized by the fact that the production of the means takes place exclusively in a Cold Procedure.

None of the prior art documents are directed to a composition presenting moisturizing properties compared to those cosmetic compositions commercially available on the market but encompassing a reduced content of emollients such as oils and esters, as well as rheological agents and humectant agents thus reducing costs and environment impact and, contrary to what was expected, the reduction of the emollients and humectant agents increased the moisturizing properties in the tests for mechanical properties of the skin.

SUMMARY OF THE INVENTION

The present invention refers to a cosmetic composition for moisturizing keratinic tissue, comprising a combination of emulsifiers which permits a reduction of the content of emollient and rheological agents in the composition and at the same time increases the sensorial moisturizing properties.

Particularly, the present invention is directed to a cosmetic composition comprising (a) an emulsifier selected from: (i) glyceryloleate citrate combined with a native oil as a viscosity modifier; or (ii) organogel comprising *Helianthus annuus* (sunflower) seed oil, polyacrylic acid, xylityl sesquicaprylate, glyceryl stearate, *Euphorbia cerifera* (candelilla) wax, sodium hydroxide and tocopherol; (b) at most 3 (three) emollient agents; (c) 01 (one) humectant agent and (d) cosmetically acceptable adjuvants.

Furthermore, the present invention is directed to the use of the cosmetic composition according to the present invention as a moisturizing agent to be used on keratinic tissue, particularly skin.

Finally, the present invention is related to a method of moisturizing keratinic tissue, particularly skin, comprising applying the cosmetic composition according to the present invention onto said keratinic tissue, particularly skin.

DETAILED DESCRIPTION OF THE INVENTION

The present invention provides a new technology involving emulsifiers to be prepared through cold processes applied in formulations for new-generation body moisturizers. The present invention refers to a minimalist formulation, which allows a reduction of emollients such as oils and esters, as well as rheological agents. Also, according to the new technology of the present invention, the content of humectant agent (for example, glycerin) in the formulations is reduced.

Such reduction of ingredients and/or contents brings as benefit minimalist compositions, with reduced environmental impact (approximately 24% for dry skin and 34% for extra-dry skin) and cost reduction.

The moisturizing efficacy of the compositions according to the present invention was studied in objective tests for evaluating the mechanical properties of the skin in different humidity conditions (20% and 50% relative humidity) and surprisingly had improved results in hydration when compared with formulations which have more emollients, oils, butters and esters and higher concentration of humectant such as glycerin.

As a consequence it was possible to provide a cosmetic composition for moisturizing keratinic tissue, using a combination of emulsifiers prepared by a cold process, thus providing minimalist formulations, reduction of the content of wetting agents, improved hydrating properties and high performance in different weather conditions.

During the development of the present invention, the emulsifier technologies were studied and the formulations were evaluated and compared with commercial available prior art moisturizers with excellent consumer acceptance.

The performance results were the following: formulations for dry and extra-dry skin using the emulsifier technology according to the present invention presented the same sensorial profile (tested trained panel) that commercial available prior art moisturizers, and allowed the reduction of the number of ingredients in the formulation; reduction of approximately 24% of the environmental impact for dry skin and 34% for extra-dry skin, all at low cost. In hydration testing the cosmetic composition according to the present invention showed superior performance results when compared to moisturizing products of the state of the art.

The cosmetic composition according to the present invention comprises:
  (e) an emulsifier selected from:
  (j) glyceryloleate citrate combined with a native oil as a viscosity modifier; or
  (ii) organogel comprising *Helianthus annuus* (sunflower) seed oil, polyacrylic acid, xylityl sesquicaprylate, glyceryl stearate, *Euphorbia cerifera* (candelilla) wax, sodium hydroxide and tocopherol;
  (f) at most 3 (three) emollient agents;
  (g) 1 (one) humectant agent and
  (h) cosmetically acceptable adjuvants.

In a preferred embodiment of the invention, the viscosity modifier combined with glyceryloleate citrate is caprylic/capric triglyceride. In a most preferred embodiment of the invention, ingredient (a)(i) is the commercially available product Dracorin GOC®.

In another embodiment of the invention, ingredient (a)(ii) is the commercially available product Emulfeel SGP®.

The content of the emulsifier in the composition according to the present patent application is from 2.0-5.0% (wt), preferably from 2.0-3.5% (wt).

In a further embodiment of the invention, the at most 3 (three) emollient agents are selected from glycerin and vegetable oils and butters. Particularly, the vegetable oils and butters are selected from: *Bertholletia excelsa* seed oil, *Butyrospermum parkii* (shea) butter, *Elaeis guineensis* (palm) oil and *Theobroma grandiflorum* seed butter.

The content of the at most 3 (three) emollient agent in the cosmetic composition according to the present invention is from −0.2-6.0% (wt), preferably from 0.4-6.0% (wt).

In a preferred embodiment, the cosmetically acceptable adjuvants are selected from viscosity modifiers, preservatives, chelating agents, stabilizing agents, lubricant agents, thickening agents, surfactants, dispersing agents, solubilizing agents, among others.

Examples of such cosmetically acceptable adjuvants are aluminum starch octenylsuccinate, Acrylates/C10-30 Alkyl Acrylate Cross-Polymer, cyclopentasiloxane, Disodium EDTA, DMDM hydantoin, Glycol Distearate (and) Coco Glucoside (and) Glyceryl Oleate (and)

Glyceryl Stearate, methylisothiazolinone, propylheptyl caprylate, sodium hydroxide 50% and xanthan gum, water, among others.

In a further embodiment of the present invention, the composition according to the present invention is used as a moisturizing agent to be used on keratinic tissue, particularly skin. Also, the invention relates to a method of moisturizing keratinic tissue by applying on the mentioned tissue the composition according to the present application.

The cosmetic composition according to the present invention provides an intelligent moisturizing power, keeps the hydration in cold/dry environment, reduces the cracking in the skin, eliminates tension in the skin, and presents an anti-stress property for the skin. The cosmetic composition of the present invention can be presented as body and/or facial lotion, moisturizer, butter, cream, serum, cream-gel.

The following examples are preferred variations of cosmetic compositions of the present invention, and should not be interpreted as being limitative of the invention. In this sense, it should be understood that the scope of the present invention encompasses other possible variations, being limited only by the content of the appended claims, possible equivalents being included therein.

EXAMPLES

Example 1

Cosmetic Composition According to the Invention for Dry Skin

| Ingredient | Content (% by weight) | Best Mode |
|---|---|---|
| Aluminum starch octenylsuccinate | 0.8-1.5 | 1 |
| Aqua or water | Qsp 100% | 82.6 |
| *Butyrospermum parkii* (shea) butter | 0.2-0.8 | 0.5 |
| Cyclopentasiloxane | 1-4 | 3 |
| Disodium EDTA | 0.05-0.1 | 0.1 |
| DMDM hydantoin | 0.1-0.6 | 0.6 |
| *Elaeis guineensis* (palm) oil PN4 | 2-6 | 4 |
| Glycerin | 3 | 3 |
| *Helianthus annuus* (sunflower) seed oil (and) polyacrylic acid (and) xylityl sesquicaprylate (and) glyceryl stearate (and) *Euphorbia cerifera* (candelilla) wax (and) sodium hydroxide (and) tocopherol. (Emulfeel SGP) | 2.5-4.5 | 3.5 |
| Glycol Distearate (and) Coco Glucoside (and)Glyceryl Oleate (and) Glyceryl Stearate | 1.0-2.0 | 1.5 |
| Methylisothiazolinone | 0.1 | 0.1 |
| Xanthan gum | 0.02-0.1 | 0.1 |
| Total | 100 | 100 |

Example 2

Cosmetic Composition According to the Invention for Extra-Dry Skin

| Ingredient | Content (% by weight) | Best Mode |
|---|---|---|
| Aluminum starch octenylsuccinate | 0.8-1.5 | 1 |
| Aqua (or) water | Qsp 100% | 80.1 |
| *Butyrospermum Parkii* (Shea) Butter | 0.2-0.8 | 1 |
| Cyclopentasiloxane | 3 | 3 |
| Disodium EDTA | 0.05-0.1 | 0.1 |
| DMDM hydantoin | 0.1-0.6 | 0.6 |
| *Elaeis guineensis* (palm) oil PN4 | 2.0-6.0 | 6 |
| Glycerin | 3 | 3 |
| *Helianthus annuus* (sunflower) seed oil (and) polyacrylic acid (and) xylityl sesquicaprylate (and) glyceryl stearate (and) *Euphorbia cerifera* (candelilla) wax (and) sodium hydroxide (and) tocopherol. (Emulfeel SGP) | 2.5-4.0 | 3.5 |
| Glycol Distearate (and) Coco Glucoside (and)Glyceryl Oleate (and) Glyceryl Stearate | 1.0-2.0 | 1.5 |
| Methylisothiazolinone | 0.1 | 0.1 |
| Xanthan gum | 0.02-0.1 | 0.1 |
| Total | 100 | 100 |

Comparative Data

Several comparative studies between the cosmetic composition according to the present invention and those from the state of the art commercially available were carried out in order to demonstrate the improved effects of the composition of the present invention.

(iii) ADQ—Quantitative Descriptive Analysis

The study aimed at describing and quantifying the sensory attributes perceived in cosmetic emulsions, through assessments by trained sensorial panel, according to the methodology of Sensorial Descriptive Analysis. The results are demonstrated in FIGS. 1A and 1B (Normal Skin), FIGS. 2A and 2B (Dry skin) and FIGS. 3A and 3B (extra-dry skin).

Figure 1A:
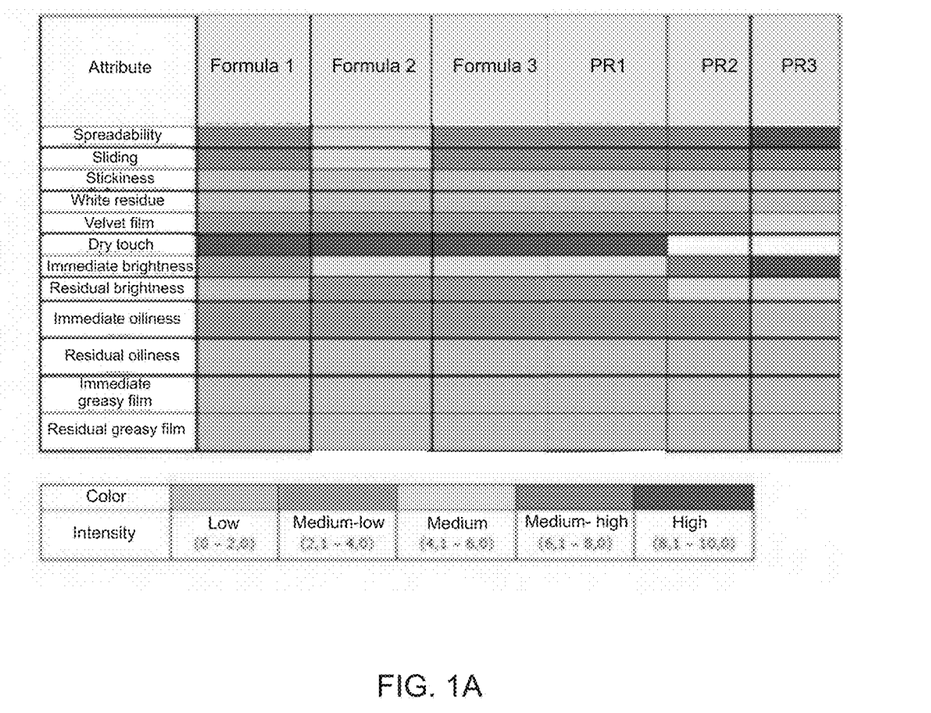
FIGS. 1A and 1B reflect the results for normal skin samples of the study aimed at describing and quantifying the sensory attributes perceived in cosmetic emulsions, through assessments by trained sensorial panel, according to the methodology of Sensorial Descriptive Analysis.
Figure 1B:
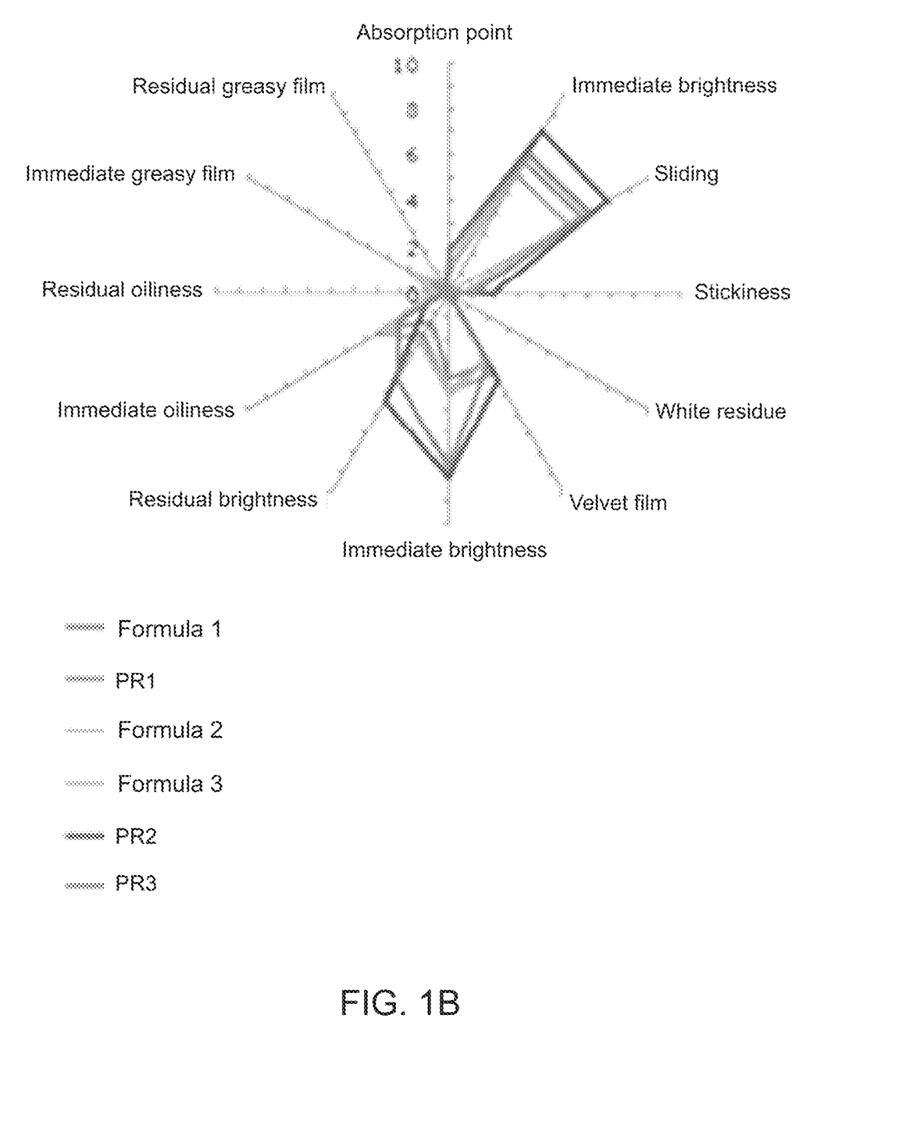

In FIGS. 1A and 1B, Formulations 1, 2 and 3 are according to the present invention and encompass Emulfeel SGP®, Lecigel® and Dracorin GOC®, respectively.

Figure 2A:
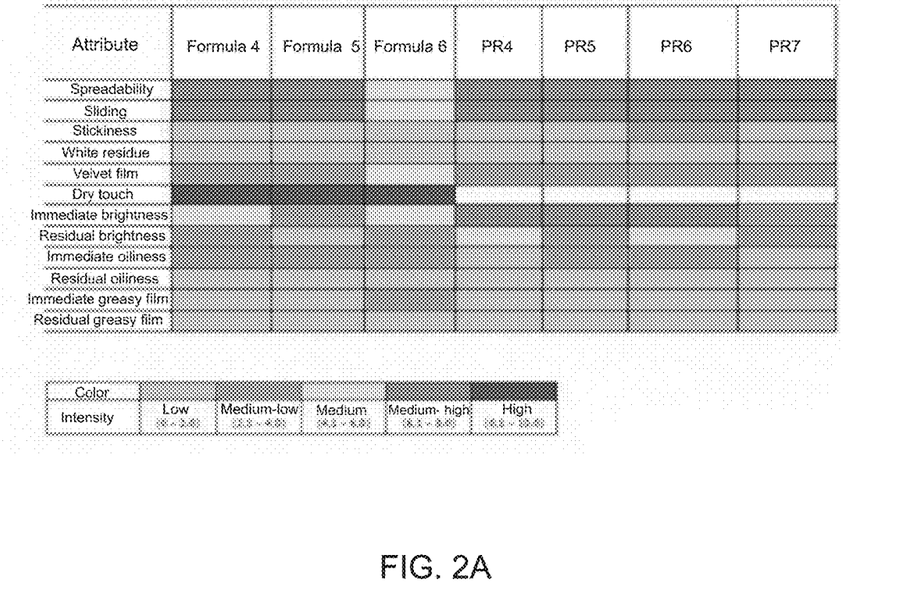
FIGS. 2A and 2B reflect the results for dry skin samples of the study aimed at describing and quantifying the sensory attributes perceived in cosmetic emulsions, through assessments by trained sensorial panel, according to the methodology of Sensorial Descriptive Analysis.
Figure 2B:
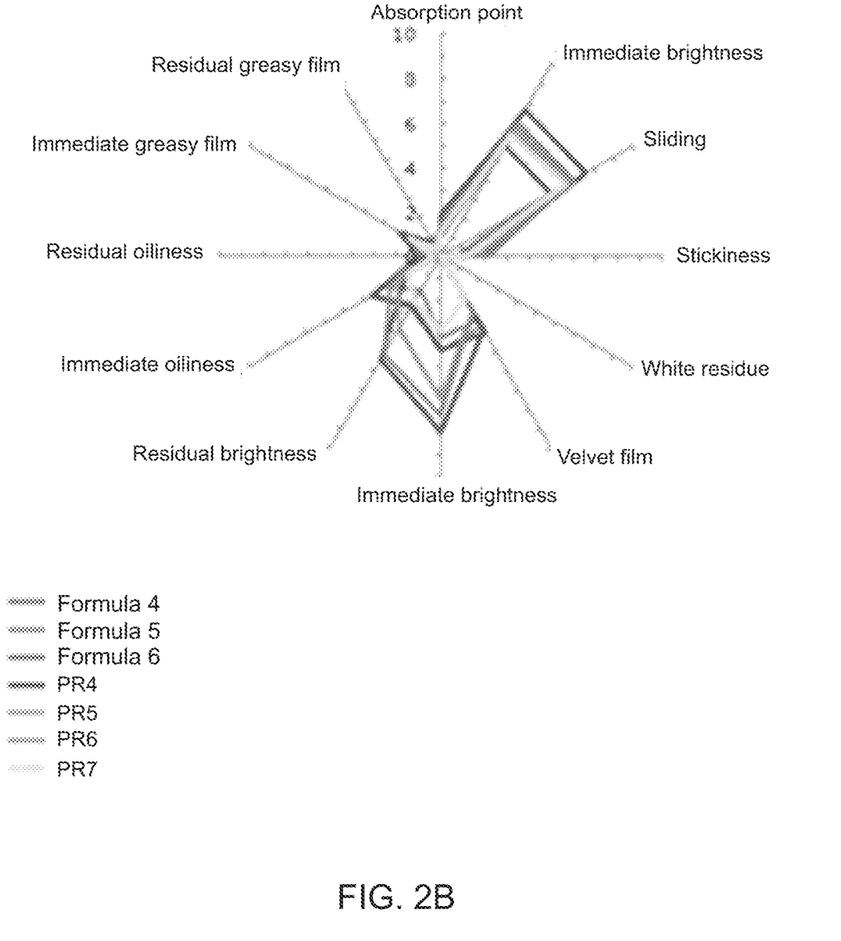

In FIGS. 2A and 2B, formulations 4, 5 and 6 are according to the present invention and encompass Dracorin GOC®, Emulfeel SGP® and Lecigel®, respectively.

Figure 3A:
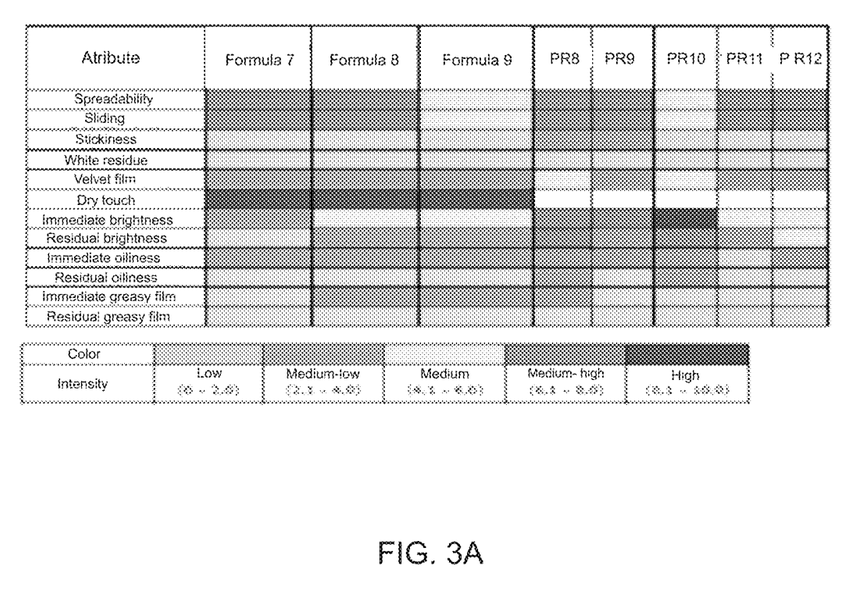
FIGS. 3A and 3B reflect the results for extra-dry skin samples of the study aimed at describing and quantifying the sensory attributes perceived in cosmetic emulsions, through assessments by trained sensorial panel, according to the methodology of Sensorial Descriptive Analysis.
Figure 3B:
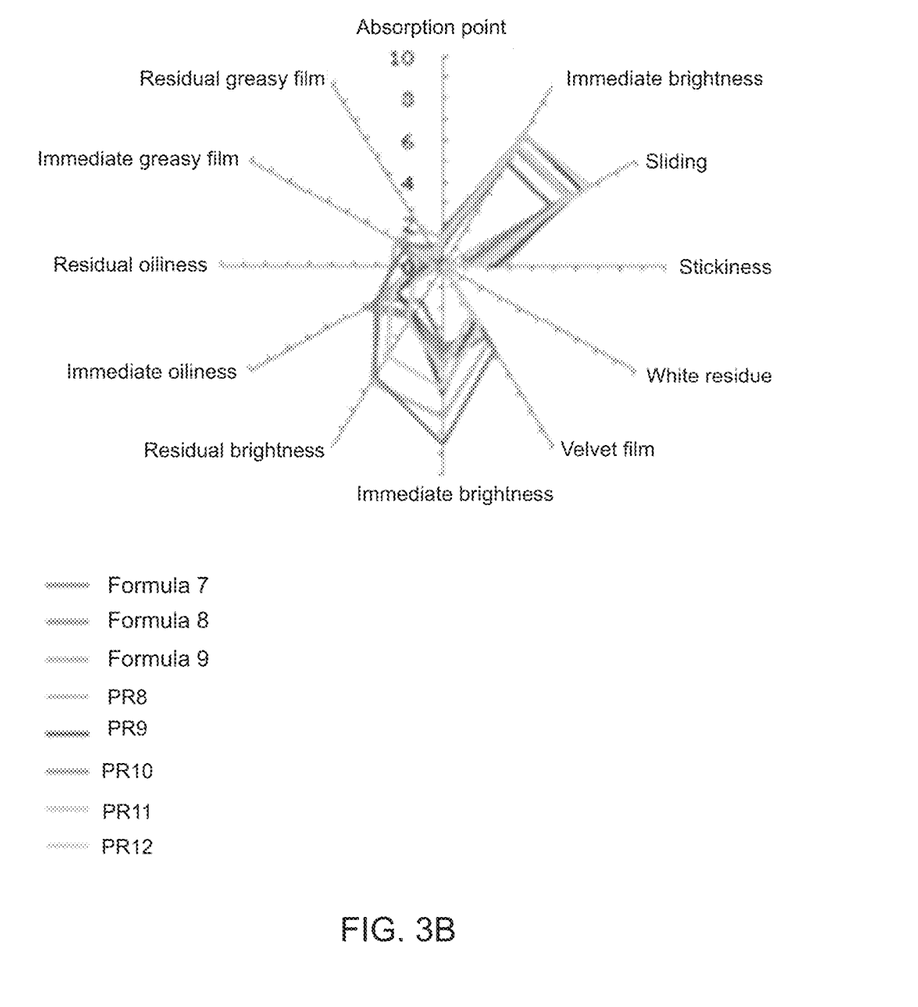

In FIGS. 3A and 3B, formulations 7, 8 and 9 are according to the present invention and encompass Emulfeel SGP®, Dracorin GOC® and Lecigel®, respectively.

From the ADQ analysis it was possible to notice that the prototypes according to the invention directed to normal, dry and extra-dry skin achieved a similar moisturizing profile when compared to the cosmetic compositions commercially available (Prior art formulations (PR) 1 to 12), but encompassing a significant reduced content of emollient and reduction of the humectant agent content in their formulae.

(iv) Evaluation of Mechanical Properties of Skin

This methodology was developed aiming to provide a new objective test to evaluate the mechanical properties of the skin in different weather conditions.

Figure 4:
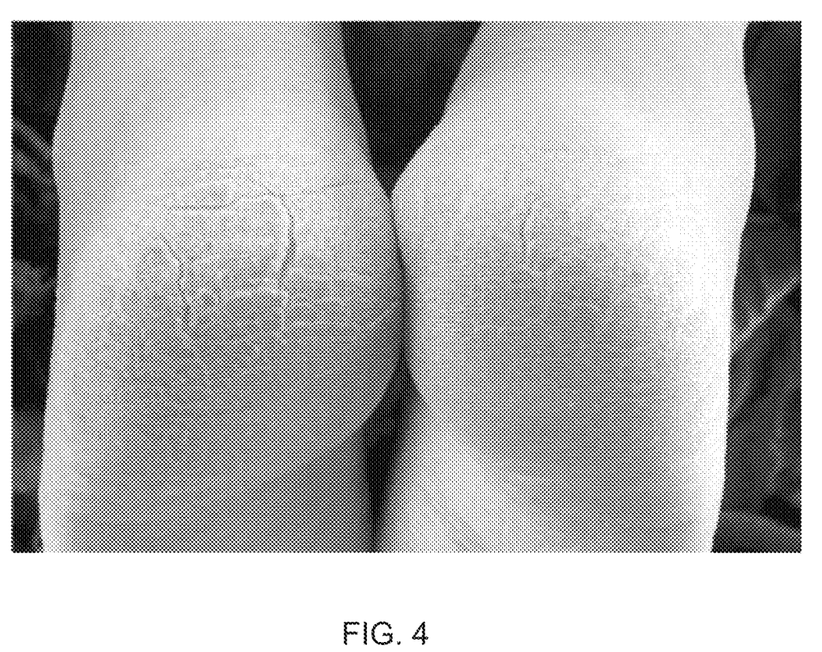
FIG. 4 discloses the appearance of a dry skin, with winter xerosis or eczema or skin dehydrated.

A healthy and hydrated skin provides good aesthetic appearance, feeling softness and elasticity, non-rigid skin (untightened skin) and surface aspects: smooth, homogeneous and velvety touch. The appearance of a dry skin, with winter xerosis or eczema or skin dehydrated can be seen in FIG. 4.

Figure 5:
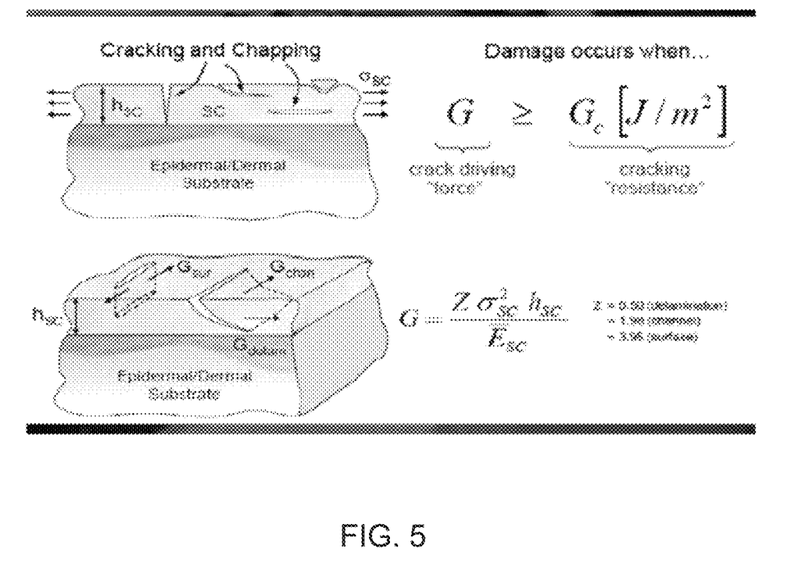
FIG. 5 discloses the mechanical models used to understand how the damage to dry skin occurs (e.g., cracks).
Figure 6:
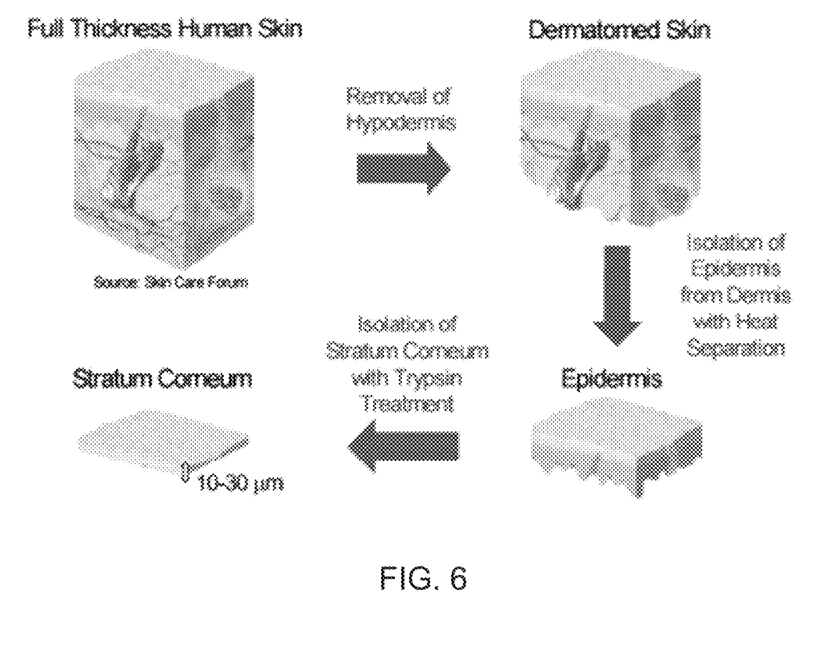
FIG. 6 discloses how the substrate is prepared.
Figure 7:
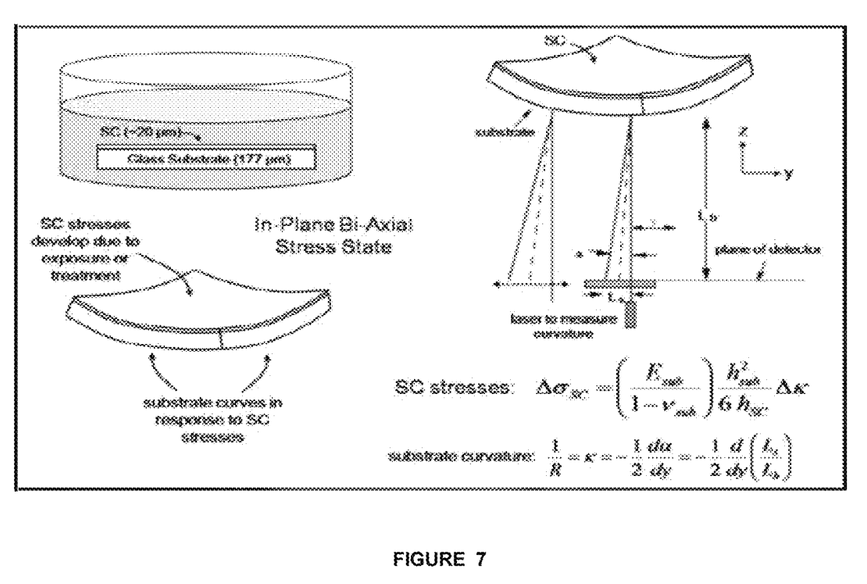
FIG. 7 discloses the determination of stress of thin films by using material science bending technique, thus characterizing the drying of the stratum corneum.

Principles Methodology: use of mechanical models to understand how the damage to dry skin occurs (e.g., cracks). Biomechanical approach considers stratum corneum (SC) as a thin film on the "substrate" epidermis+dermis (FIG. 5). The substrate is prepared according to FIG. 6. To characterize the drying of the SC was used as material science bending technique for the determination of stress of thin films (FIG. 7).

The products tested were: Formulation according to the invention (Inv. 1) (cosmetic composition for normal skin according to the present invention) and Formulation according to the invention (Inv. 2) (cosmetic composition for dry skin according to the present invention) and.

Figure 8:
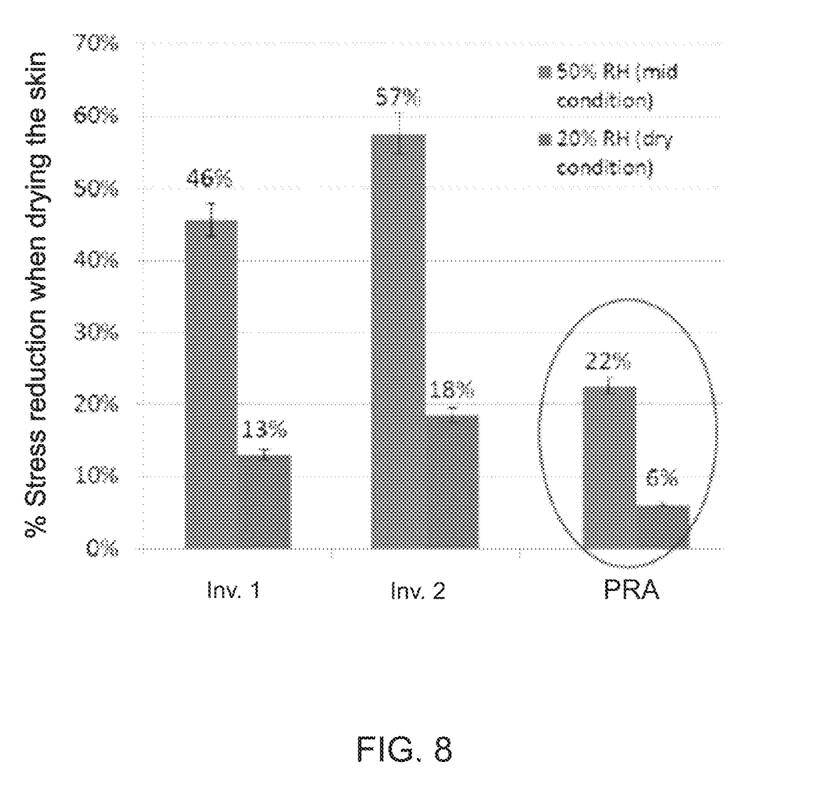
FIGS. 8, 9 and 10 disclose the results obtained in the evaluation of the mechanical Properties of the Skin.
Figure 9:
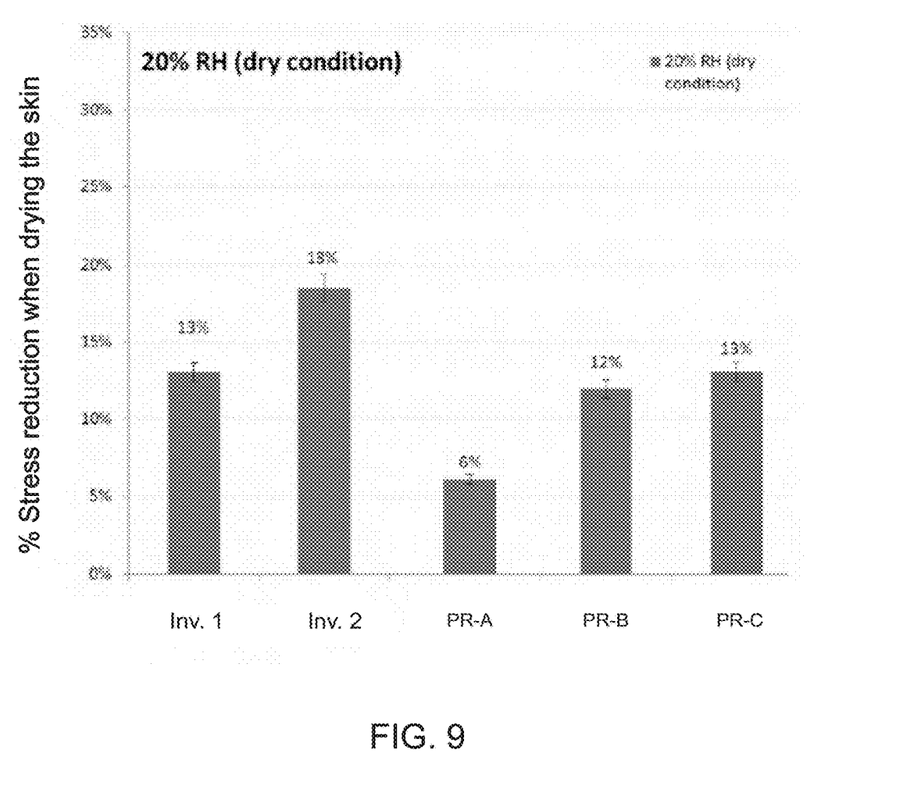
Figure 10:
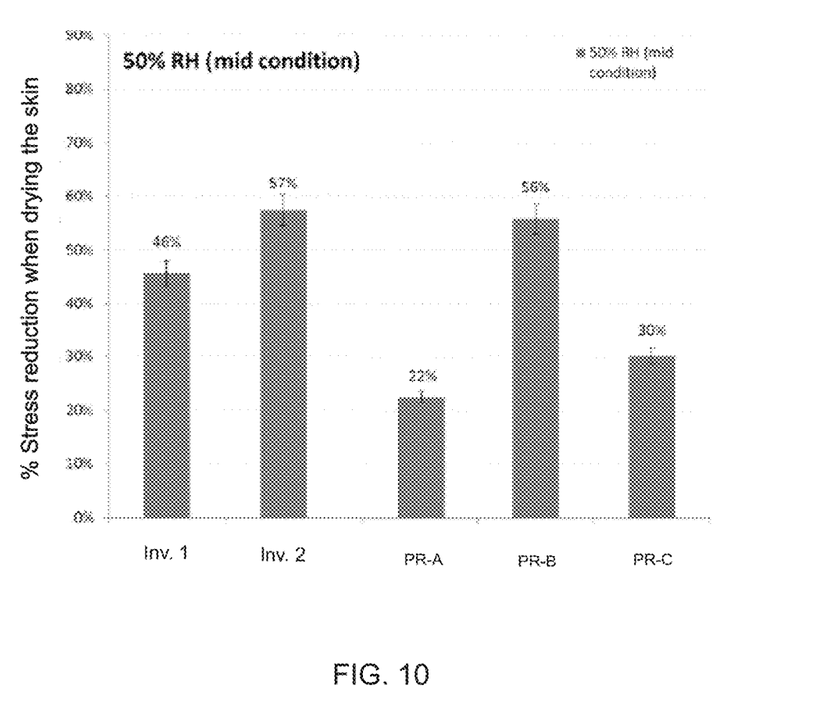

The results obtained in the evaluation of the mechanical Properties of the Skin can be observed in FIGS. 8, 9 and 10. In such Figures, PR-A is a prior art formulation comprising a higher number of emollients and a higher glycerin content. PR-B and PR-C are body oils from the prior art.

The cosmetic composition according to the present invention tested according to the above described method showed very positive results and demonstrated intelligent hydration, retention of moisture in cold/dry weather, protection of the skin in any situation, reduced propensity to cracking, elimination skin tension and anti-stress properties for the skin.

The invention claimed is:

1. A composition for reducing cracking of skin and improving hydration of skin in a human consisting essentially of therapeutically effective amounts of cyclopentasiloxane, shea butter, aluminum starch octenylsuccinate, palm oil, sunflower seed oil and candelilla wax.

\* \* \* \* \*